(12) United States Patent
Palmer, Jr.

(10) Patent No.: US 9,051,341 B2
(45) Date of Patent: Jun. 9, 2015

(54) REACTIVE SURFACTANTS FOR EMULSION POLYMERIZATION, PIGMENT DISPERSION, AND UV COATINGS

(75) Inventor: Charles Francis Palmer, Jr., Greer, SC (US)

(73) Assignee: ETHOX CHEMICALS LLC, Greenville, SC (US)

( * ) Notice: Subject to any disclaimer, the term of this patent is extended or adjusted under 35 U.S.C. 154(b) by 336 days.

(21) Appl. No.: 13/598,437

(22) Filed: Aug. 29, 2012

(65) Prior Publication Data

US 2013/0047892 A1    Feb. 28, 2013

Related U.S. Application Data

(60) Provisional application No. 61/573,084, filed on Aug. 29, 2011.

(51) Int. Cl.

| | | |
|---|---|---|
| *C08K 5/06* | (2006.01) | |
| *C08F 222/40* | (2006.01) | |
| *C07F 9/09* | (2006.01) | |
| *C07C 43/23* | (2006.01) | |
| *C07C 309/10* | (2006.01) | |
| *C08G 65/14* | (2006.01) | |
| *C08G 65/26* | (2006.01) | |
| *C09D 171/02* | (2006.01) | |
| *C08G 65/334* | (2006.01) | |
| *C08G 65/335* | (2006.01) | |
| *C08K 3/22* | (2006.01) | |
| *C08K 5/41* | (2006.01) | |
| *C08K 5/521* | (2006.01) | |

(52) U.S. Cl.
CPC .............. *C07F 9/091* (2013.01); *C07C 43/23* (2013.01); *C07C 309/10* (2013.01); *C08K 3/22* (2013.01); *C08K 5/41* (2013.01); *C08K 5/521* (2013.01); *C08G 65/14* (2013.01); *C08G 65/2612* (2013.01); *C09D 171/02* (2013.01); *C08G 65/3344* (2013.01); *C08G 65/3355* (2013.01)

(58) Field of Classification Search
USPC ....................................................... 524/366
See application file for complete search history.

(56) References Cited

U.S. PATENT DOCUMENTS

| | | | | |
|---|---|---|---|---|
| 4,221,685 A | * | 9/1980 | Eschwey et al. ............. | 106/252 |
| 4,814,514 A | * | 3/1989 | Yokota et al. ................ | 568/608 |
| 6,841,655 B1 | * | 1/2005 | Gota et al. .................... | 528/425 |

FOREIGN PATENT DOCUMENTS

JP          2002-301353 A          10/2002

* cited by examiner

*Primary Examiner* — Hui Chin
(74) *Attorney, Agent, or Firm* — Isaac A. Angres

(57) ABSTRACT

The present invention provides reactive surfactants of the formula

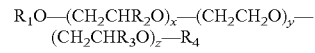

where $R_1$ is either alkyl, aryl, alkylaryl, or aralkylaryl of 8-30 carbon atoms, $R_2$ is —$CH_2OCH_2CH$=$CH_2$ (AGE); $R_3$ is either H, $CH_3$, or $CH_2CH_3$; $R_4$ is H or —$SO_3M$ or —$PO_3M$ where M is H or K, Na, $NH_4$, $NR_4$, alkanolamine, or other cationic species and x=2-100; y=4-200 and z=0-50.

9 Claims, 6 Drawing Sheets

Figure 2
(1 day)

Figure 3
(2 days)

Figure 4
(4 days)

Figure 5

(Stains on untreated pine board)

Figure 6

(Contact angle measurements of water drops on stained pine board)

Example 2

Example 31

Example 30

Example 29

Example 2 with Aqua Bead

Example 29 with Aqua Bead

US 9,051,341 B2

REACTIVE SURFACTANTS FOR EMULSION POLYMERIZATION, PIGMENT DISPERSION, AND UV COATINGS

This application claims the priority benefit under 35 U.S.C. section 119 of U.S. Provisional Patent Application No. 61/573,084 entitled "Reactive Surfactants For Emulsion Polymerization, Pigment Dispersion, And UV Coatings" filed on Aug. 29, 2011, and which is in its entirety herein incorporated by reference.

FIELD OF THE INVENTION

The present invention relates to emulsion polymerizing ethylenically unsaturated monomers. This invention also relates to emulsion polymerization of ethylenically unsaturated monomers by using styrenated surfactants containing multiple allyl glycidyl ether groups as the primary emulsifier. The instant invention also relates to a process for the preparation of a polymer dispersion by free radical polymerization of an aqueous monomer emulsion. The present invention further relates to a method for production of waterborne polymer and copolymer dispersions comprising monomer units derived from at least one polymerizable ethylenically unsaturated monomer. The polymer and copolymer dispersions are obtained in a free radical emulsion polymerization process performed in an aqueous media and in the presence of at least one styrenated surfactant containing multiple allyl glycidyl ether groups. In a further aspect, the present invention refers to the use of said polymer or copolymer dispersion.

BACKGROUND OF THE INVENTION

Emulsion polymerization is the most important industrial method for manufacture of aqueous dispersion polymers. Emulsion polymerization is typically performed in an aqueous medium in the presence of a surfactant and a water-soluble initiator and usually rapidly produces high molecular weight homo or copolymers at high solids content and low dispersion viscosity. Its application requires the emulsification of the monomer in a medium, usually water, through the use of emulsifiers. These are supplied in addition to the other ingredients that go into most polymerizations, such as the initiator and chain transfer agents. The use and type of emulsifier determines many of the characteristics of the produced polymer or copolymer, which is typically a latex (stable colloidal suspension of polymer particles in a continuous phase, usually water). Moreover, the emulsifier usually cannot be completely removed from the latex. For this reason, and because of the great unpredictability of the efficacy of a given surface-active agent as an emulsifier in polymerization, many compounds that would theoretically be useful are not.

It is also known that emulsion polymerization requires the use of a surfactant to form a stable emulsion of monomers and to prevent coagulation of the product polymer. Surfactants are generally categorized into two types: either non-polymerizable, or polymerizable, that is co-polymerizable with the monomers for polymer formation. Surfactants are also categorized as anionic, cationic, non-ionic or zwitterionic depending on their chemical makeup. A problem which has arisen with the use of non-polymerizable surfactants is that they remain as a residue in the product polymer and, as they can be extracted by water, they make the product sensitive to water.

The name "emulsion polymerization" is a misnomer that arises from a historical misconception. Rather than occurring in emulsion droplets, polymerization takes place in the latex particles that form spontaneously in the first few minutes of the process. These latex particles are typically 100 nm in size, and are made of many individual polymer chains. The particles are stopped from coagulating with each other because each particle is surrounded by the surfactant ('soap'); the charge on the surfactant repels other particles electrostatically. When water-soluble polymers are used as stabilizers instead of soap, the repulsion between particles arises because these water-soluble polymers form a 'hairy layer' around a particle that repels other particles, because pushing particles together would involve compressing these chains.

Emulsion polymerization is used to manufacture several commercially important polymers. Many of these polymers are used as solid materials and must be isolated from the aqueous dispersion after polymerization. In other cases the dispersion itself is the end product. A dispersion resulting from emulsion polymerization is often called a latex (especially if derived from a synthetic rubber) or an emulsion (even though "emulsion" strictly speaking refers to a dispersion of an immiscible liquid in water). These emulsions find applications in adhesives, paints, paper coating and textile coatings. They are finding increasing acceptance and are preferred over solvent-based products in these applications as a result of their eco-friendly characteristics due to the absence of VOCs (Volatile Organic Compounds) in them.

Advantages of emulsion polymerization include:

High molecular weight polymers can be made at fast polymerization rates. By contrast, in bulk and solution free radical polymerization, there is a tradeoff between molecular weight and polymerization rate.

The continuous water phase is an excellent conductor of heat and allows the heat to be removed from the system, allowing many reaction methods to increase their rate.

Since polymer molecules are contained within the particles, the viscosity of the reaction medium remains close to that of water and is not dependent on molecular weight.

The final product can be used as is and does not generally need to be altered or processed.

The resulting latex is typically used in coating applications such as paints, stains, etc. Once the latex-containing product has been applied to a surface as part of a protective or decorative coating, the surfactant is no longer needed. In fact, the presence of the surfactant often degrades the moisture sensitivity of the coating. Other coating properties such as adhesion to the substrate surface can be negatively affected as well. This is largely due to the mobility of the surfactant polymers. For example, locally high concentrations of surfactant molecules can form in the coating from the coalescence of surfactant-coated micelle spheres. When the coating is exposed to water, these unbound surfactant molecules can be extracted from the coating leaving thin spots or pathways to the substrate surface. This can result in a pinholing effect and attack of the substrate by water.

Reactive surfactants contain a polymerizable moiety that can participate in free-radical emulsion polymerization reactions. When used in an emulsion polymerization a large fraction of the surfactant molecules become irreversibly bound to the emulsion polymer chains and droplets. When the latex is then incorporated into a coating such as paint, there is much less free surfactant to interfere with the desired coating properties or to reduce adhesion to the substrate.

A number of reactive nonionic and anionic surfactants are commercially available, including polyoxyethylene alkylphenyl ethers, sodium allyloxy hydroxypropyl sulfonates, alkenyl-functional nonionic surfimers, allyl methoxy triethylene glycol ether, sodium methallyl sulfonates, sulfopropyl acrylate, vinyl sulfonate, vinyl phosphate, monosodium ethylsulfonate monododecyl maleate, sorbitol acrylate, sorbitol methacrylate, perfluoroheptoxy poly(propyloxy)methacrylate, phenoxyl poly(ethyleneoxy acrylate, phenoxyl poly(ethyleneoxy)methacrylate, nonyl phenoxy poly(ethyleneoxy) crotanate, nonylphenoxy poly(ethyleneoxy)fumarate, nonyl phenoxy poly(ethyleneoxy)acrylate, nonylphenoxy poly(ethyleneoxy)methacrylate, mono dodecyl maleate, and allylsulfosuccinate derivatives.

Additionally, anionic reactive surfactants have been disclosed in Japanese Patent Publication No. 46-12472, Japanese Kokai Patent Publication No. 54-144317, Japanese Patent Publication No. 46-34894, Japanese Patent Publication No. 56-29657, Japanese Kokai Patent Publication No. 51-30285, U.S. Pat. No. 4,814,514, and U.S. Pat. No. 5,324,862 among others. A review of reactive surfactants may be found in "Reactive Surfactants in Emulsion Polymerization" Guyot, A. and Tauer, K., in *Advances in Polymer Science*, Vol III, Springer-Verlag, Berlin, pp 43-65.

None of these reactive surfactants incorporate more than one reactive moiety in their structure. In fact, the styrenated phenol-based materials disclosed in U.S. Pat. No. 4,814,514 prepared by the addition of allyl glycidyl ether (AGE) to surfactant base molecules such as hydroxyl-functional fatty alcohols or substituted phenols specifically limit the amount of AGE to 1.0 mole.

SUMMARY OF THE INVENTION

The instant invention provides an improved class of reactive surfactants, both nonionic and anionic depicted in Formulas I-IV below, for use in both conventional aqueous emulsion polymers, as pigment dispersants, and in coatings for UV curing. These new reactive surfactants are copolymers of two or more moles of allyl glycidyl ether (AGE) and ethylene oxide terminated on one end with a hydrophobic moiety. The addition of a second equivalent of AGE significantly reduces the amount of non-reactive surfactant in the product so that increases in coating repellency may be achieved.

The reactive surfactant of formula (I) is an anionic surfactant of structure:

(I)

where $R=CH_3$, $CH_2CH_3$, $C_6H_5$, or $C_{14}H_{29}$; n=1, 2, or 3; x is 2-10, y is 0-200, z is 4-200, more preferably from about 5 to 60, and most preferably from about 5 to 40; Z can be either $SO_3^-$ or $PO_3^{2-}$, and $M^+$ is $Na^+$, $K^+$, $NH_4^+$, or an alkanolamine.

The present invention is further directed towards the emulsion polymerization of ethylenically unsaturated monomers in the presence of a nonionic surfactant of formula (II)

(II)

where $R=CH_3$, $CH_2CH_3$, $C_6H_5$, or $C_{14}H_{29}$; n=1, 2, 3; x is 2-10, y is 0-200, z is 4-200, more preferably from about 5 to 60, and most preferably from about 5 to 40.

The instant invention also further includes anionic and nonionic surfactants of Formula III and IV:

(III)

where $R_1$ is a $C_{10-24}$ alkyl, alkaryl, alkenyl, or cycloalkyl, $R_2=CH_3$, $CH_2CH_3$, $C_6H_5$, or $C_{14}H_{29}$; x is 2-10, y is 0-200, z is 4-200, more preferably from about 5 to 60, and most preferably from about 5 to 40; and Z can be either $SO_3^-$ or $PO_3^{2-}$, and $M^+$ is $Na^+$, $K^+$, $NH_4^+$, or an alkanolamine.

(IV)

where $R_1$ is a $C_{10-24}$ alkyl, alkaryl, alkenyl, or cycloalkyl, $R_2=CH_3$, $CH_2CH_3$, $C_6H_5$, or $C_{14}H_{29}$; x is 2-10, y is 0-200, z is 4-200, more preferably from about 5 to 60, and most preferably from about 5 to 40.

These new reactive surfactants may contain various hydrophobes such as styrenated phenol ethers, alkyl ethers such as tridecyl alcohol, or alkylphenol ethers. Varying the level of ethoxylation or propoxylation and adjusting the size of the hydrophobe results in being able to tune the structure for optimal performance.

Other monomers may be included in the copolymer along with AGE and EO. These include propylene oxide (PO) and other epoxides such as 1,2-butylene oxide, styrene oxide, or 1,2-tetradecane oxide.

These nonionic copolymers may be optionally further derivatized to convert them to anionic surfactants. Examples of these include sulfonates, phosphate esters, carboxylates, and sulfosuccinates.

These new surfactants impart improved properties to coatings for wood deck stains and direct-to-metal coatings obtained with these novel surfactants. These properties include low particle size, improved water repellency, freeze-thaw stability, improved gloss, water resistance, and other ink and coating properties.

Generally, the latex particles are prepared by mixing monomers together to form a monomer mixture. A surfactant or surfactants is (are) then added to the monomer mixture and added to water with mixing to form an emulsion. The surfactant(s) may include a reactive surfactant, a nonreactive surfactant, or a combination of reactive and nonreactive surfactants. In one embodiment of the invention, nonreactive surfactants can be used to form the latex particle, and reactive surfactants can be used, either in concert or added in a second step. Alternatively, polymerization can be carried out as a soap-free polymerization, with a reactive surfactant being added near the end of polymerization.

DETAILED DESCRIPTION OF THE INVENTION

The present invention is directed to novel reactive surfactants, the use of the surfactants in emulsion polymerization and the use of the resulting compositions.

The invention provides reactive surfactants having the following formulas:

(I)

where $R=CH_3$, $CH_2CH_3$, $C_6H_5$, or $C_{14}H_{29}$; $n=1$, 2, or 3; x is 2-10, y is 0-200, z is 4-200, more preferably from about 5 to 60, and most preferably from about 5 to 40; Z can be either $SO_3^-$ or $PO_3^{2-}$, and $M^+$ is $Na^+$, $K^+$, $NH_4^+$, or an alkanolamine;

(II)

where $R=CH_3$, $CH_2CH_3$, $C_6H_5$, or $C_{14}H_{29}$; $n=1$, 2, 3; x is 2-10, y is 0-200, z is 4-200, more preferably from about 5 to 60, and most preferably from about 5 to 40;

(III)

where $R_1$ is a $C_{10-24}$ alkyl, alkaryl, alkenyl, or cycloalkyl, $R_2=CH_3$, $CH_2CH_3$, $C_6H_5$, or $C_{14}H_{29}$; x is 2-10, y is 0-200, z is 4-200, more preferably from about 5 to 60, and most preferably from about 5 to 40; and Z can be either $SO_3^-$ or $PO_3^{2-}$, and $M^+$ is $Na^+$, $K^+$, $NH_4^+$, or an alkanolamine; and (IV)

where $R_1$ is a $C_{10-24}$ alkyl, alkaryl, alkenyl, or cycloalkyl, $R_2=CH_3$, $CH_2CH_3$, $C_6H_5$, or $C_{14}H_{29}$; x is 2-10, y is 0-200, z is 4-200, more preferably from about 5 to 60, and most preferably from about 5 to 40.

The reactive surfactants are manufactured by reacting one equivalent of either the di- or tri-styrenated phenol or other hydroxyl containing materials with 2 or more equivalents of allyl glycidyl ether in an autoclave using potassium hydroxide catalyst at a temperature in the range of 100-110 C to produce an adduct having at least two equivalents of allyl glycidyl ether. The resulting adduct is then reacted with an alkylene oxide, mixtures of alkylene oxides and styrene oxide in the presence of a basic catalyst such as potassium hydroxide or an alkali metal alkoxide such as sodium or potassium methoxide.

More specifically the process for alkoxylation includes the steps of: adding the catalyst to the organic compound containing at least one hydroxyl group; heating and pressurizing a reactor containing the hydroxyl containing organic compound; supplying alkylene oxide to said organic compound and catalyst at a process temperature of between 50° and 250° C. and at a pressure of between 100 and 700 kPa and isolating the alkoxylation products.

The alkylene oxides useful for the alkoxylation reaction are selected from the group consisting of ethylene oxide, propylene oxide, butylenes oxide, $C_5$-$C_{18}$ oxides and styrene oxide. The alkylene oxide groups may be arranged at random or in blocks. Particular preference is given to block arrangements with fairly hydrophobic groups such as propylene oxide or, butylene oxide. The ratio of the molar amounts of the ethylene oxide groups to the other hydrophobic alkylene oxide groups is adjusted as necessary to achieve the desired properties.

The performance properties of the novel reactive surfactants of the invention may be optimized for a specific application by appropriate modification such as the degree of alkoxylation and the different alkylene oxides that are used, and the choice of group used as an end cap. The interplay between these factors appears to be complex and is not well-understood. However, it is clear that manipulation of these variables allows access to materials which can perform as excellent emulsifiers.

The present invention is also directed towards the emulsion polymerization of ethylenically unsaturated monomers in the presence of an anionic surfactant of formula (I)

(I)

where R=$CH_3$ or $CH_2CH_3$, n=1, 2, 3; x is 2-10, y is 0-200, z is 4-200 more preferably from about 5 to 60, and most preferably from about 5 to 40; Z can be either $SO_3^-$ or $PO_3^{2-}$, and $M^+$ is $Na^+$, $K^+$, $NH_4^+$, or an alkanolamine.

The present invention also provides emulsion polymerization of ethylenically unsaturated monomers in the presence of a nonionic surfactant of formula (II)

(II)

where R=$CH_3$ or $CH_2CH_3$, n=1, 2, 3; x is 2-10, y is 0-200, z is 4-200 more preferably from about 5 to 60, and most preferably from about 5 to 40.

In another embodiment, the present invention is further directed towards the emulsion polymerization of ethylenically unsaturated monomers in the presence of a surfactant of formulae (III) or (IV).

(III)

where $R_1$ is a C10-24 alkyl, alkaryl, alkenyl, or cycloalkyl, $R_2$=$CH_3$, $CH_2CH_3$, C6H5, or $C_{14}H_{29}$; x is 2-10, y is 0-200, z is 4-200, more preferably from about 5 to 60, and most preferably from about 5 to 40. Z can be either $SO_3^-$ or $PO_3^{2-}$, and $M^+$ is $Na^+$, $K^+$, $NH_4^+$, or an alkanolamine;

(IV)

where R1 is a C10-24 alkyl, alkaryl, alkenyl, or cycloalkyl, $R_2$=$CH_3$, $CH_2CH_3$, $C_6H_5$, or $C_{14}H_{29}$; x is 2-10, y is 0-200, z is 4-200, more preferably from about 5 to 60, and most preferably from about 5 to 40.

The compounds of formulas (I)-(IV) may be used separately or in combination in the emulsion polymerization. When used in combination, the ratio of compounds of formulae (I) to (IV) is not limited but is dictated by the desired emulsion properties. Surfactants of formulas (I) to (IV) may also be used in combination with other surfactants that are commonly used in the art When used in combination, the ratio of surfactants is not specific but is commonly optimized based on the nature of the ethylenically unsaturated monomers present in a given formulation. The total amount of surfactants of formulas (I) to (IV) that may be used in the present invention is preferably from about 0.1% to about 20% based on total weight of the monomer, more preferably from about 0.2% to about 10%, and most preferably from about 0.5% to about 7% based on the total weight of the monomer. The compounds of formulas (I) to (IV) may also be used in combination with conventional surfactants in order to improve emulsion properties.

Other surfactants that are commonly used in the emulsion polymerization process include both anionic and nonionic molecules. Commonly utilized anionic surfactants in the emulsion polymerization process include sodium alkylbenzene sulfonates, alkyldiphenyloxide disulfonates, ethoxylated alkylphenol sulfates and phosphates, alkyl sulfosuccinates, and sulfates and phosphates of fatty alcohols, etc. Commonly utilized nonionic surfactants include linear and branched alcohol ethoxylates, and alkylphenol ethoxylates, particularly octylphenol ethoxylates. When used in combination with other surfactants the ratios are not limited but are also dictated by the desired emulsion properties.

Suitable monomers that may be polymerized by the practice of the present invention include numerous ethylenically unsaturated monomers such as vinyl monomers or acrylic monomers. Typical vinyl monomers suitable for use in accordance with the present invention include, but are not limited to, vinyl esters such as vinyl acetate, vinyl propionate, vinyl benzoate, etc; vinyl aromatic hydrocarbons such as styrene, methyl styrenes, other vinyl aromatics such as vinyl toluenes, vinyl napthalenes, divinyl benzene, etc. Halogenated vinyl monomers such as vinyl chloride, vinylidene chloride, etc. may also be used.

Suitable acrylic monomers which may be used in accordance with the present invention comprise compounds with acrylic functionality such as alkyl acrylates and methacrylates, acrylate acids and methacrylate acids as well as acrylamides and acrylonitrile. Typical acrylic monomers include, but are not limited to methyl acrylate and methyl methacrylate, ethyl, propyl, and butyl acrylate and methacrylate, benzyl acrylate and methacrylate, cyclohexyl acrylate and methacrylate, decyl and dodecyl acrylate and methacrylate, etc. Other typical acrylic monomers include hydroxy alkyl acrylates and methacrylates such as hydroxypropyl and hydroxyethyl acrylate and methacrylate, acrylic acids such as methacrylic and acrylic acid, and amino acrylates and methacrylates. It will be recognized by those familiar with the art that other unsaturated monomers which are suitable for free radical addition polymerization may also be used in accordance with the present invention.

Numerous free radical forming compounds are utilized as catalysts in the emulsion polymerization process. Typically compounds used as catalysts are those that from free radicals via thermal decomposition, referred to in the art as "thermal initiators" or combinations of compounds that form free radicals via oxidation/reduction reactions. Such catalysts are combinations of an oxidizing agent and a reducing agent and are commonly referred to in the art as "redox initiators." Either thermal or redox catalysts may be used in the practice of the present invention.

Typical catalysts utilized as thermal initiators include persulfates, specifically potassium persulfate, sodium persulfate, ammonium persulfate and the like. Typical redox initiators include combinations of oxidizing agents or initiators such as peroxides, specifically benzoyl peroxide, t-butyl hydroperoxide, lauryl peroxide, hydrogen peroxide, 2,2'-diazobisiso-butyronitrile, and the like. Typical reducing agents include sodium bisulfite, sodium formaldehyde sulfoxylate, sodium hydrosulfite, and ascorbic and isoascorbic acid. The catalyst or initiator is employed in an amount preferably from 0.1 to 3 weight percent of the total monomer weight, and most preferably from about 0.1 to 1 weight percent of the total monomer charge.

Other additives or components which are known to those skilled in the art may also used in accordance with the present invention. These include chain transfer agents, which are used to control molecular weight, additives to adjust pH, and compounds utilized as protective colloids which provide additional stability to the latex particles.

The typical ingredients used in an emulsion polymerization are listed in the following generalized recipe:

| Component | %-Wet Basis |
| --- | --- |
| Monomers | 30-50 |
| Surface-active agents | 1-3 |
| Protective colloid | 0-3 |
| Initiator | 1-3 |
| Modifier | 0-1 |
| Buffer | 0-1 |
| Water | 50-70 |

The emulsifiers suspend monomer droplets and polymer particles. Modifiers may be aldehydes, mercaptans or chlorinated hydrocarbons that control the polymerization reaction restricting cross-linking and controlling the molecular weight. Protective colloids, such as polyvinyl alcohol or methyl cellulose, are used to stabilize the final latex. Buffer salts control the pH of the emulsion polymerization batch. These salts, such as phosphates, citrates, acetates and carbonates, are important because pH affects reaction rate, particle size and other reaction conditions.

In some cases the monomer emulsion is seeded with polymer particles. The purpose of seeded emulsion polymerization is to avoid the uncertainties of the particle initiation stage, obtain better batch-to-batch reproducibility, and give a stable latex of the desired particle size. The reasons for polymerizing in water include: more rapid polymerization than bulk polymerization at the same temperature with a greater average molecular weight; good heat transfer in water with better control of heat of polymerization; all of the monomer is consumed in the polymerization and the resulting latex can be used directly in coating applications; and the aqueous phase lowers the overall viscosity of the emulsion.

The monomer emulsion is made up of water-immiscible monomer droplets stabilized by surfactant molecules, empty micelles (colloidal surfactant vesicles) and monomer-swollen micelles. The monomer droplets can range in size from less than one micrometer to ten micrometers. The size of micelles is about 10 to 15 nanometers. During the reaction, the monomer molecules diffuse from the droplet reservoirs to the micelles where polymerization takes place. The polymer chains grow in the micelles. As polymerization proceeds, the monomer droplets decrease in size and eventually disappear. When the polymer particles become large, the surfactant molecules in the micelles suspend the polymer particles. The final polymer particles grow to a size range of a few tenths of a micrometer up to one micrometer. The physical character of the final polymer depends on the temperature of reaction, the formulation and the manipulation of the reaction conditions, such as when and how much of the ingredients are added to the reactor.

A homogenizer is used in emulsion polymerization to emulsify the monomer into the premix to the reactor. Of all the emulsion monomers, vinyl chloride polymerization is the one that most commonly uses homogenizers to prepare the mix. In a typical process the ingredients to make the polymer are added in the appropriate sequence to an evacuated, agitated, pressurized tank (pressurized with nitrogen gas). After mixing the ingredients and adjusting the temperature of the mix, the emulsion is homogenized to produce the desired monomer droplet size. The homogenizing pressure may be in the range of 1000 to 5000 psi, depending on the monomer and the required droplet size of the monomer reservoir. This monomer droplet size can affect the physical character of the final latex particles. From the homogenizer the emulsion goes to the reactor, where polymerization occurs at a controlled temperature, until the desired conversion is achieved. After completion of the reaction, the latex is cooled and removed from the reactor.

Any other of the conventional methods employed in the emulsion polymerization process may also be used in accordance with the present invention. These include both standard and pre-emulsion monomer addition techniques as well as staged monomer addition.

The invention further provides pigment dispersions suitable for preparation of coating compositions wherein a pigment is finely and stably dispersed in a high concentration in aqueous and non-aqueous solvent for applications in industrial fields of inks, paints, stains, pigmented photoresists and the like.

More specifically the invention also provides a pigment dispersion comprising: (a) a pigment; (b) a solvent; and (c) a dispersing surfactant the formulas I-IV as described above.

The pigment of the dispersion of the present invention may be selected from inorganic pigments (such as carbon black pigments, e.g., furnace blacks, electrically conductive carbon black pigments, extender pigments and corrosion inhibitive pigments); organic pigments; dispersed dyes; and mixtures thereof. Examples of organic pigments that may be present in the pigment dispersion include, but are not limited to, perylenes, phthalo green, phthalo blue, nitroso pigments, manoazo pigments, diazo pigments, diazo condensation pigments, basic dye pigments, alkali blue pigments, blue lake pigments, phloxin pigments, quinacridone pigments, lake pigments of acid yellow 1 and 3, carbozole dioxazine violet pigments, alizarine lake pigments, vat pigments, phthaloxy amine pigments, carmine lake pigments, tetrachloroisoindolinone pigments and mixtures thereof. Inorganic pigments that may be present in the pigment dispersion, include, for example, titanium dioxide, electrically conductive titanium dioxide, and iron oxides, e.g., red iron oxides, yellow iron oxides, black iron oxides and transparent iron oxides. Extender pigments that may be present in the pigment dispersion include, but are not limited to, silicas, clays, alkaline earth metal sulfates and carbonates, such as calcium sulfate, magnesium sulfate, barium sulfate, and calcium carbonate. The pigment dispersion may contain corrosion inhibitive pigments, such as aluminum phosphate and calcium modified silica. Mixtures of organic and inorganic pigments are also suitable for making the dispersions of the present invention.

The pigments may have average primary particle diameter of 8 to 80 nm, preferably 10 to 35 nm, and a DBP number of 40 to 200 ml/100 g, preferably 60 to 150 ml/100 g, can be used as the carbon black. In a preferred embodiment of the invention, gas blacks with an average primary particle diameter of 8 to 30 nm, preferably 10 to 25 nm, can be used.

EXAMPLES

The present invention is illustrated by the following Examples, but should not be construed to be limited thereto. In the Examples, "part" and "%" are all part by weight or % by weight unless specified otherwise.

Example 1

Manufacture of Surfactant

Distyrenated phenol (DSP) (694 g, 1 equivalent) was added to a stainless steel autoclave along with allyl glycidyl ether (AGE) (494 g, 2 equivalents) and potassium hydroxide KOH (2.3 g) and the autoclave sealed and heated to 105 C. When all of the AGE was consumed, the reaction mass was cooled, and the product discharged. This is AGE 2 DSP adduct.

1680 g of this AGE 2 DSP adduct (1 equivalent) was added to another autoclave and heated to 105 C. Ethylene oxide (2026 g, 15 equivalents) was then added over the course of several hours. After all of the EO was consumed, the reaction mass was cooled and the catalyst neutralized with the addition of a small amount of acid. This material is Example 1.

Example 1A

Distyrenated phenol (DSP) (1388 g, 2 equivalent) was added to a stainless steel autoclave along with allyl glycidyl ether (AGE) (988 g, 4 equivalents) and potassium hydroxide KOH (4.6 g) and the autoclave sealed and heated to 105 C. When all of the AGE was consumed, the reaction mass was cooled, and the product discharged. This is AGE 2 DSP adduct.

3360 g of this AGE 2 DSP adduct (2 equivalents) was added to another autoclave and heated to 105 C. Ethylene oxide (4052 g, 30 equivalents) was then added over the course of several hours. After all of the EO was consumed, the reaction mass was cooled and the catalyst neutralized with the addition of a small amount of acid.

Example 1B

Distyrenated phenol (DSP) (347 g, 0.5 equivalent) was added to a stainless steel autoclave along with allyl glycidyl ether (AGE) (247 g, 1 equivalents) and potassium hydroxide KOH (1.15 g) and the autoclave sealed and heated to 105 C. When all of the AGE was consumed, the reaction mass was cooled, and the product discharged. This is AGE 2 DSP adduct.

940 g of this AGE 2 DSP adduct (0.5 equivalent) was added to another autoclave and heated to 105 C. Ethylene oxide (1013 g, 7.5 equivalents) was then added over the course of several hours. After all of the EO was consumed, the reaction mass was cooled and the catalyst neutralized with the addition of a small amount of acid.

Example 1C

Distyrenated phenol (DSP) (2776 g, 4 equivalent) was added to a stainless steel autoclave along with allyl glycidyl ether (AGE) (1976 g, 8 equivalents) and potassium hydroxide KOH (9.2 g) and the autoclave sealed and heated to 105 C. When all of the AGE was consumed, the reaction mass was cooled, and the product discharged. This is AGE 2 DSP adduct.

6720 g of this AGE 2 DSP adduct (4 equivalents) was added to another autoclave and heated to 105 C. Ethylene oxide (8104 g, 60 equivalents) was then added over the course of several hours. After all of the EO was consumed, the reaction mass was cooled and the catalyst neutralized with the addition of a small amount of acid.

Example 2

Example 1 was sulfated with sulfamic acid in a glass reactor equipped with a stirrer, thermometer, and reflux condenser by heating to 120 C until the % sulfate was >90%. The product was isolated as the ammonium salt.

Example 3

Three moles of Example 1 was phosphated with one mole of phosphorus pentoxide ($P_2O_5$) in a glass reactor equipped with a stirrer, thermometer, and reflux condenser by heating to 70 C until the reaction was complete. The product phosphoric acid ester, a mixture of mono- and diesters, was neutralized with aqueous ammonium hydroxide. The product was isolated as the ammonium salt in aqueous solution.

In a procedure similar to Examples 1, 2, or 3, examples 4-24 were prepared:

Examples 4-24

| Example No. | Hydrophobe | AGE (equivalents) | EO (equiv) | Terminal group |
|---|---|---|---|---|
| 4 | DSP | 1 | 16 | —OH |
| 5 | DSP | 1 | 16 | —$OSO_3^-$ $NH_4^+$ |
| 6 | DSP | 2 | 15 | —$OSO_3^-$ $NH_4^+$ |
| 7 | DSP | 2 | 15 | —$OPO_3^-$ $NH_4^+$ |
| 8 | DSP | 2 | 15 | —$OPO_3^-$ $K^+$ |
| 9 | Tridecyl alcohol | 1 | 17 | —OH |
| 10 | Tridecyl alcohol | 1 | 17 | —$OSO_3^-$ $NH_4^+$ |
| 11 | Tridecyl alcohol | 2 | 36 | —OH |
| 12 | Tridecyl alcohol | 2 | 36 | —$OPO_3^-$ $NH_4^+$ |
| 13 | Nonylphenol | 2 | 4 | —OH |
| 14 | Nonylphenol | 2 | 4 | —$OSO_3^-$ $NH_4^+$ |
| 15 | Nonylphenol | 2 | 38 | —OH |
| 16 | Nonylphenol | 2 | 38 | —$OSO_3^-$ $NH_4^+$ |
| 17 | DSP | 2 | 15 | —$OPO_3^-$ $NH_4^+$ |
| 18 | DSP | 1 | 5 | —OH |
| 19 | DSP | 1 | 5 | —$OSO_3^-$ $NH_4^+$ |
| 20 | DSP | 2 | 5 | —$OSO_3^-$ $NH_4^+$ |
| 21 | TSP | 1 | 10 | —OH |

| Example No. | Hydrophobe | AGE (equivalents) | EO (equiv) | Terminal group |
|---|---|---|---|---|
| 22 | TSP | 1 | 10 | —OSO3− NH4+ |
| 23 | TSP | 2 | 10 | —OH |
| 24 | TSP | 2 | 10 | —OSO3− NH4+ |

TSP is tristyrenated phenol, a mixture of mono-, di-, and tristyrenated phenol with the major component tristyrenated phenol
DSP is distyrenated phenol, a mixture of mono-, di-, and tristyrenated phenol with the major component distyrenated phenol Examples 25-28

Latex Resistance to Water Penetration

All latex Examples 25-28 were produced in a jacketed glass reactor using the recipe below. Each example varied only on the surfactant used in the latex preparation.

| Example | Latex Polymerization Surfactant |
|---|---|
| 25 | Example 5 |
| 26 | Example 2 |
| 27 | POE(4) nonylphenol sulfate, NH4 salt (non-reactive surfactant control) |
| 28 | POE(10) allyl-substituted nonylphenol sulfate, NH4 salt |

The temperature was regulated by an external circulating water heater. The reactor was fitted with a thermocouple and feed lines. The monomer was fed subsurface through a stainless steel tube. The initiator (oxidizer and reducer) were added above the surface of the latex. Both monomer and initiator were pumped into the reaction solution.

Latex Recipe:

| Material | Weight | Purity | Solids |
|---|---|---|---|
| Initial Charge | | | |
| Example 5 | 46.40 | 0.25 | 11.60 |
| Sodium bicarbonate | 10.00 | 1.00 | 10.00 |
| Water | 973.60 | 0.00 | 0.00 |
| Sub Total | 1030.00 | | 21.60 |
| Initial Oxidizer | | | |
| Ammonium Persulfate | 4.00 | 1.00 | 4.00 |
| Water (DI) | 12.00 | 0.00 | 0.00 |
| Sub Total | 16.00 | | 4.00 |
| Monomer Feed | | | |
| water | 386.80 | 0.00 | 0.00 |
| Example 5 | 23.20 | 0.25 | 5.80 |
| VV10* | 700.00 | 1.00 | 700.00 |
| Butyl acrylate (BA) | 200.00 | 1.00 | 200.00 |
| Methyl methacrylate (MMA) | 460.00 | 1.00 | 460.00 |
| Methacrylic acid (MAA) | 20.00 | 1.00 | 20.00 |
| Sub Total | 1790.00 | | 1385.80 |
| Delayed Oxidizer | | | |
| Ammonium Persulfate | 4.00 | 1.00 | 4.00 |
| Water | 100.00 | 0.00 | 0.00 |
| Sub Total | 104.00 | | 4.00 |
| Post Oxidizer | | | |
| t-butylhydroperoxide (tBHP) | 1.50 | 0.70 | 1.05 |
| Water | 40.00 | 0.00 | 0.00 |
| Sub Total | 41.50 | | 1.05 |
| Post Reducer | | | |
| Sodium metabisulfite (SMBS) | 1.50 | 1.00 | 1.50 |
| Water | 40.00 | 0.00 | 0.00 |
| Sub Total | 41.50 | | 1.50 |
| Post Addition | | | |
| NH4OH (28% NH3) | 5.00 | 0.00 | pH = 8 |
| Water (DI) | 0.00 | 0.00 | 0.00 |
| Sub Total | 5.00 | | 0.00 |
| TOTAL SUM | 3028.0 | | 1418.0 |

| Feed rates | Start | Stop | Rate (mls/min) |
|---|---|---|---|
| Monomer Feed 1 | 0 | 180 | 9.9 |
| Delayed Oxidizer | 0 | 180 | 0.58 |
| Post Oxidizer | 180 | 240 | 0.69 |
| Post Reducer | 180 | 240 | 0.69 |
| Residual monomers | | | |
| MMA | BA | Sty | VV10 | Vinyl A |

| Expected properties | |
|---|---|
| Total Solids (%) | 46.8% |
| Surfactant on solids | 1.23% |
| Oxidizer on solids | 0.64% |
| Reducer on solids | 0.11% |
| Measured properties | |
| Total Solids (%) | |
| Filterable solids - 40 150 mesh | |
| pH | |
| Viscosity | |
| Particle size - 10% 50% 90% | |
| Particle size - Mv | |
| Mn | |
| Ma | |

*Vinyl Versatate (VV10 - Momentive)

Procedure:
1. Start circulating water heaters
2. Make up initial and delayed oxidizer solutions
3. Make up initial charge
4. Make up monomer feed in the order presented
5. Add initial charge
6. Raise temperature to 80 C.
7. Add initial oxidizer.
8. Begin monomer feed
9. Begin delayed oxidizer feed
10. At end of feed, wait 1 hour
11. Begin post oxidizer and post reducer over 60 minutes.
12. Remove heat and allow to cool.
13. Adjust pH
14. Measure properties Five millimeter thick films of each of the latexes 25-28 were cast onto both glass and Leneta sheets and allowed to fully dry. Then a drop of water was placed on the dried latex film and covered with an inverted beaker to prevent evaporation. After standing for 24 hours, the resistance to water whitening (blushing) of the dried latex film was checked.

More whitening or haziness indicated more water uptake by the latex film. Water uptake is undesirable for a protective coating.

Figure 1:
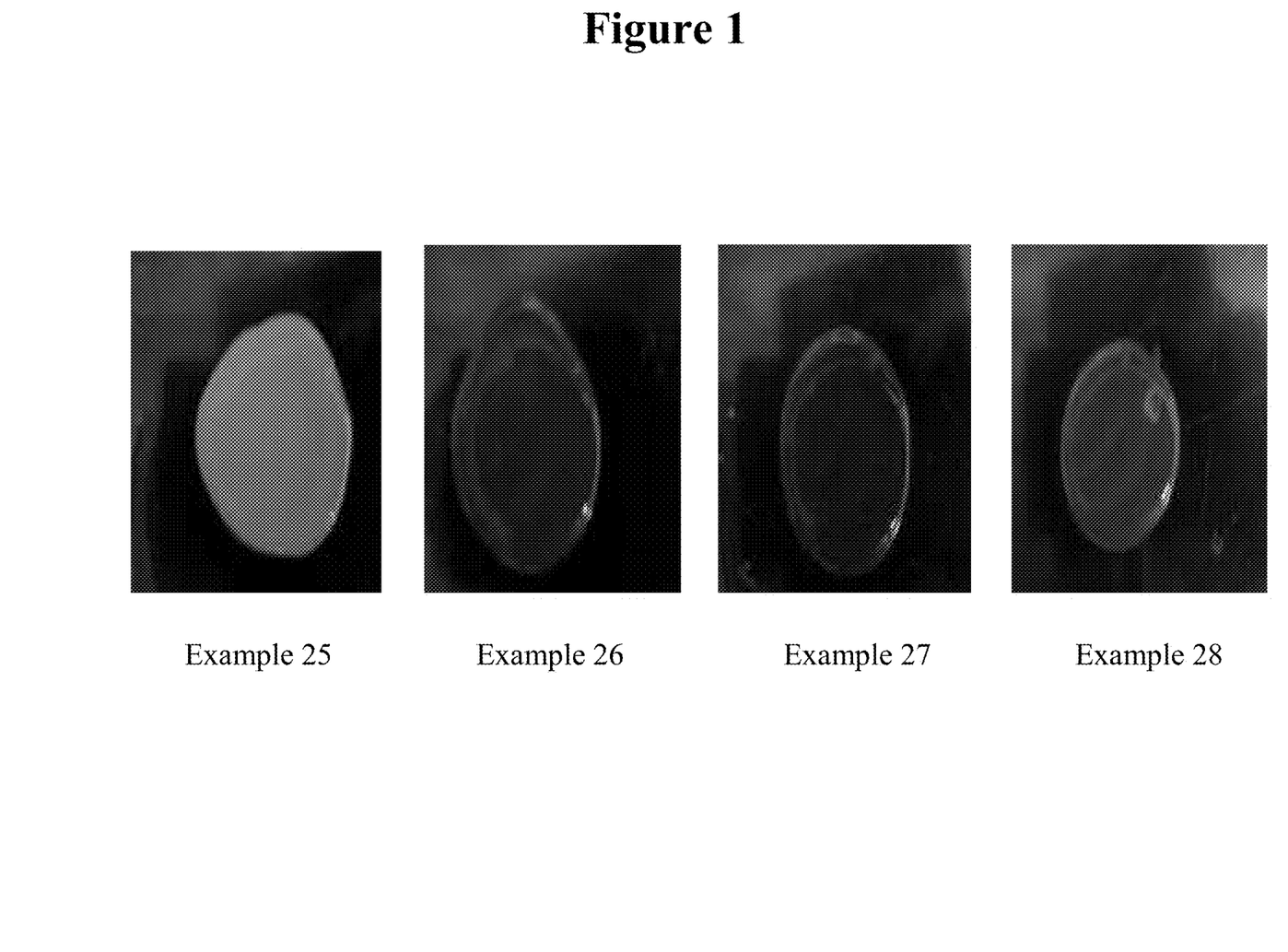
FIG. 1 illustrates the water soak test results.

The following table indicates the relative amount of whitening by each of the dried latex films on glass after water exposure. This is shown visually in FIG. 1.

TABLE 1

| Example | Description | Drawdown | | Water whitening | | |
|---|---|---|---|---|---|---|
| | | Glass | Leneta | Glass | Leneta | Rank |
| 25 | One reactive group (Example 6) | Slightly hazy | Slightly hazy | Very hazy | Very hazy | 4 (worst) |
| 26 | Two reactive grp (Example 2) | Slightly hazy | Slightly hazy | Very slightly white | Very slightly white | 1 (best) |
| 27 | No reactive grp (control) | Slightly hazy | Slightly hazy | slightly white | slightly white | 2 |
| 28 | One reactive grp (control) | Slightly hazy | Slightly hazy | slightly white | slightly white | 3 |

A study similar to the water drop test was performed by soaking dried samples in water. The samples were cast over polyethylene sheeting and allowed to dry for 4 days, turning the samples over each day to aid in the drying process. The final sample thickness was ⅛ inch. These samples were then placed in 600 ml beakers and covered with 200 ml of water.

Figure 2:
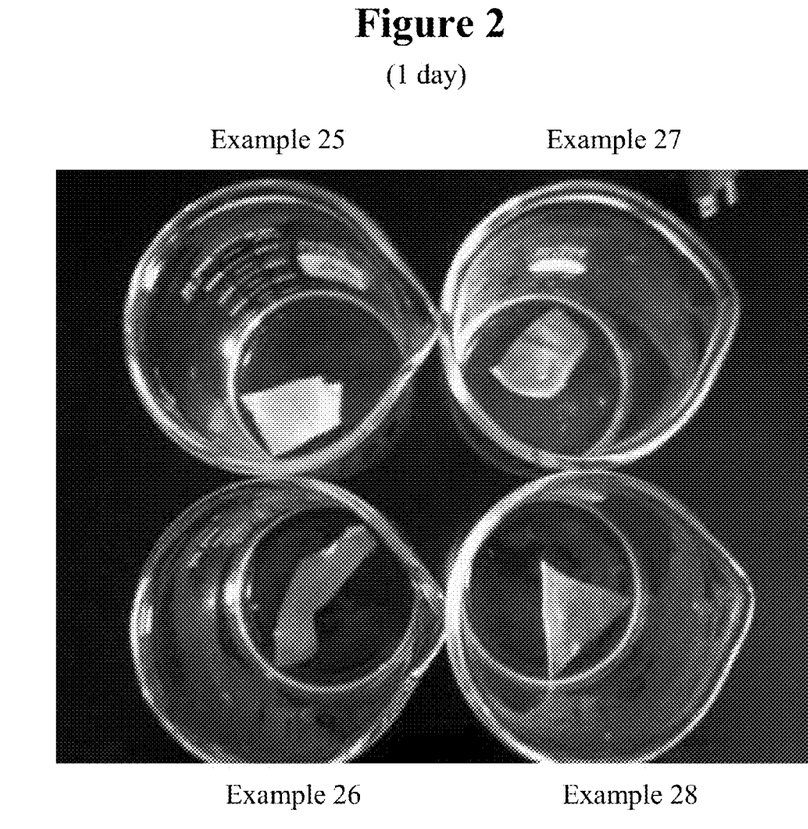
FIG. 2 shows the water uptake as measured by change in opacity after one day.
Figure 3:
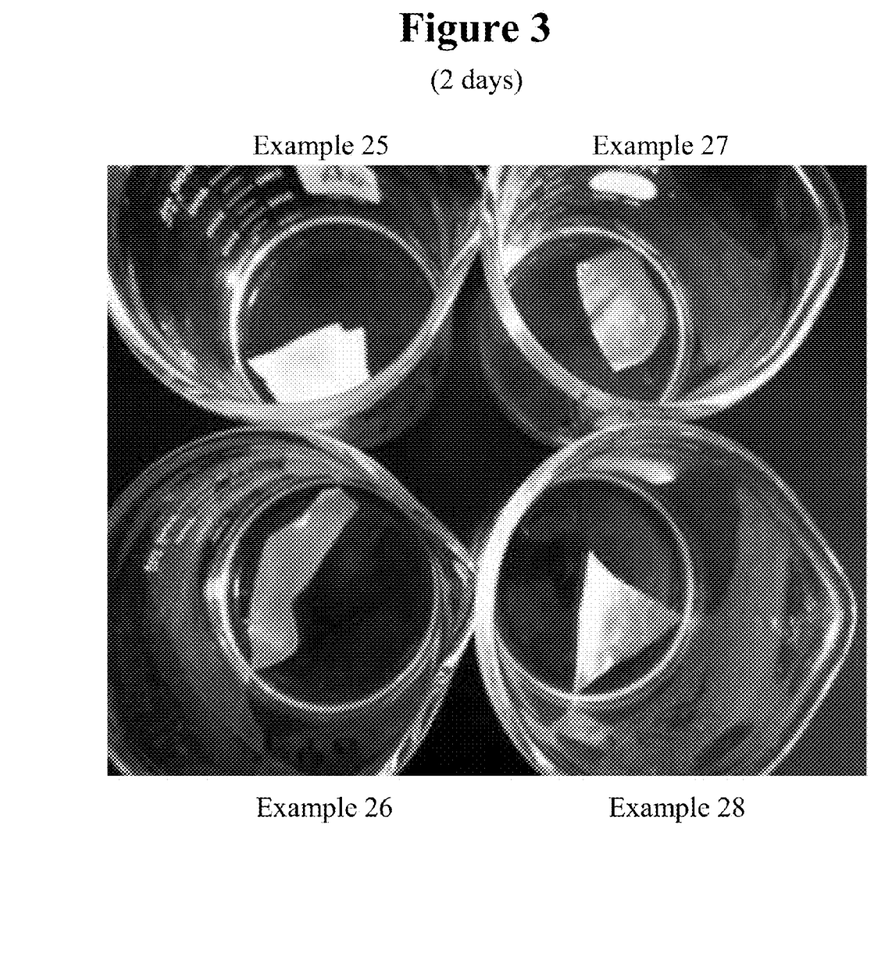
FIG. 3 describes the water uptake as measured by change in opacity after two days.
Figure 4:
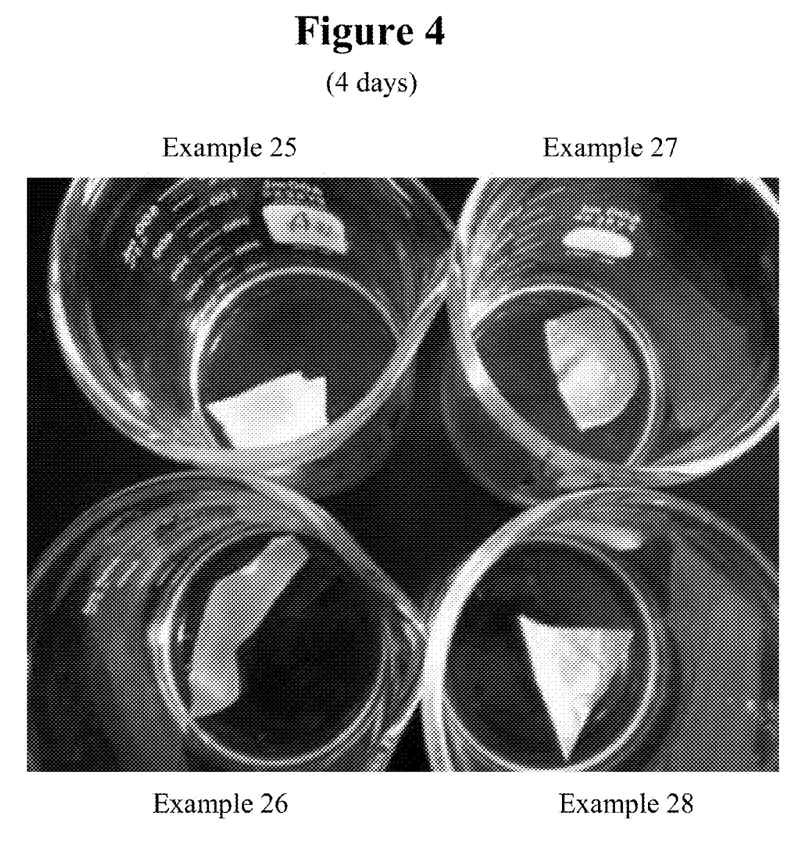
FIG. 4 illustrates the water uptake as measured by change in opacity after four days.

Example 26, the latex incorporating the surfactant with two reactive groups (Example 2), has the best blush resistance of the four latexes studied as determined by the least water whitening. The latex in Example 25, based on the Example 5 surfactant with the same structure and polyethylene oxide chain length as the Example 2 surfactant but with only one reactive group, was the poorest in water resistant properties. These two surfactants have much longer polyethylene oxide chains (which increase water whitening) than the Example 27 and 28 surfactants. Nevertheless, Example 26 with two reactive groups and a long polyethylene oxide chain showed better performance than both surfactants with one reactive group (Ex 25 and 28) and better than Example 27 incorporating the very short polyethylene oxide chain surfactant. Water uptake as measured by change in opacity was noted as a function of time (1 day, 2 days, and 4 days). Whiter films indicate higher water sensitivity of the latexes. The data is presented below in FIGS. 2, 3, and 4 respectively.

No further changes were noted after the 4 days of soaking. The order of water whitening (water sensitivity) is as follows and correlates well with the water spot test:
Most Ex25>Ex28>Ex27>Example 26 Least
Deck Stain Formulations with Reactive Surfactants The Examples 25-28 latexes were formulated into deck stains.

TABLE 2

(Surfactants used in this study)

| Example | Surfactant |
|---|---|
| 29 | POE(4) nonylphenol sulfate, ammonium salt |
| 30 | POE(10) allyl-substituted nonylphenol sulfate, NH$_4$ salt |
| 31 | Ex 5 POE(16) {DSP/1 AGE} Sulfate |
| 32 | Ex 2 POE(15) {DSP/2 AGE} Sulfate |

Experimental Procedure for Deck Stain Formulation:

The formulation procedure for the deck stain is shown below

| Ingredients | #1 | #2 |
|---|---|---|
| Examplel Latex | 97.5 | 97.5 |
| Water | 111.2 | 111.2 |
| Byk 023[1] | 0.1 | 0.1 |
| TINT-AYD CW 5600 Transparent RedOxide[2] | 1.2 | 1.2 |
| Aqua Bead 525[3] | 0.0 | 2.5 |
| Butyl CARBITOL Solvent[4] | 1.7 | 1.7 |
| Total | 211.7 | 214.2 |
| Latex Solids | 41.9 | |
| Coalescing Level, phr | 4.1 | |
| Total Solids, % by weight | 17.7 | |
| by volume | 16.3 | |
| Weight per Gallon, lb. | 8.5 | |

[1]BYK-Chemie
[2]Elementis Specialties
[3]Michelman
[4]DOW

The ingredients were added to a stainless steel beaker in the order listed above under agitation. The paint was mixed for a further 15 minutes. The paint was stored in ½ pint cans.

Figure 5:
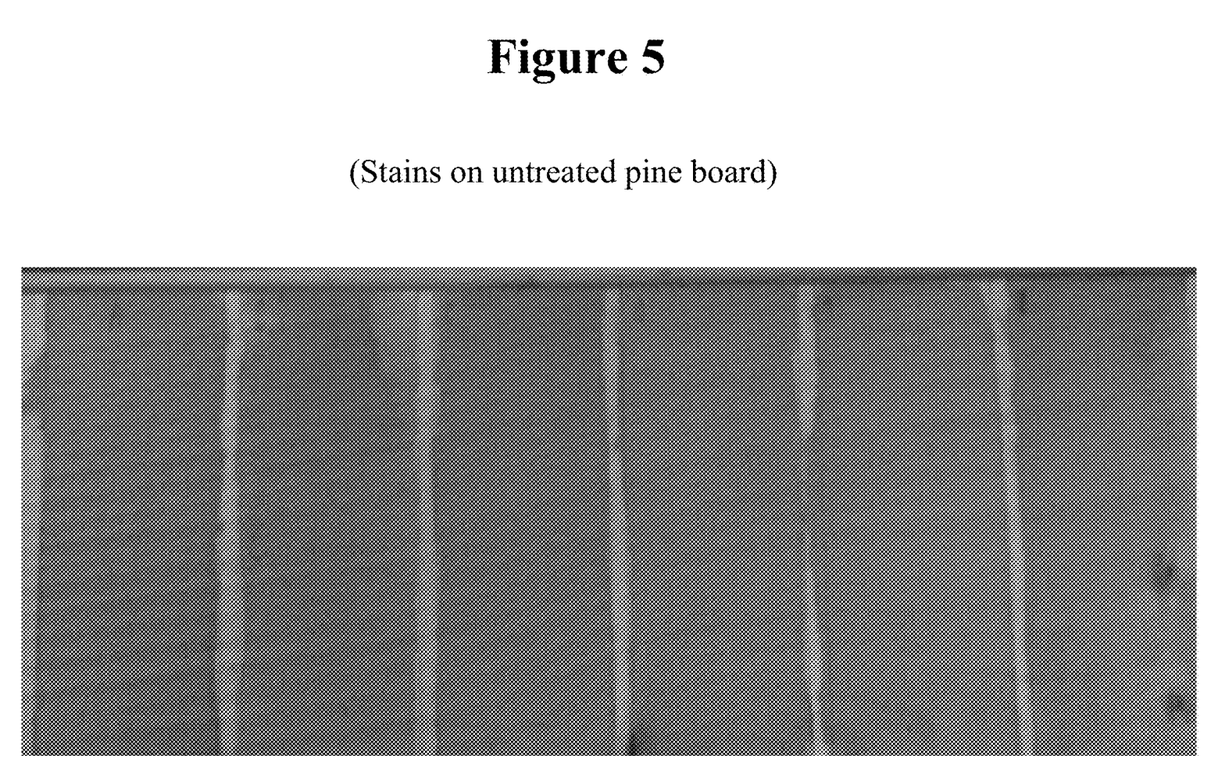
FIG. 5 shows stains on an untreated pine board.

Paints were made with Aqua Bead 525 wax using latexes made from POE(4) nonylphenol sulfate, ammonium salt and Example 2 in order to determine the effects of this ingredient on water beading properties as a function of surfactant type.
Effect of Surfactant Type on Water Beading Deck stain performance is often demonstrated through its ability to produce water beads when sprayed with water. Latexes which are more hydrophobic in nature provide superior water beading. In order to determine the water beading character of the latexes which were formulated into deck stains, the stains were applied to a southern yellow pine board. Three grams of stain was applied to a 3×5" area of the wood and allowed to dry overnight (See FIG. 5).

Figure 6:
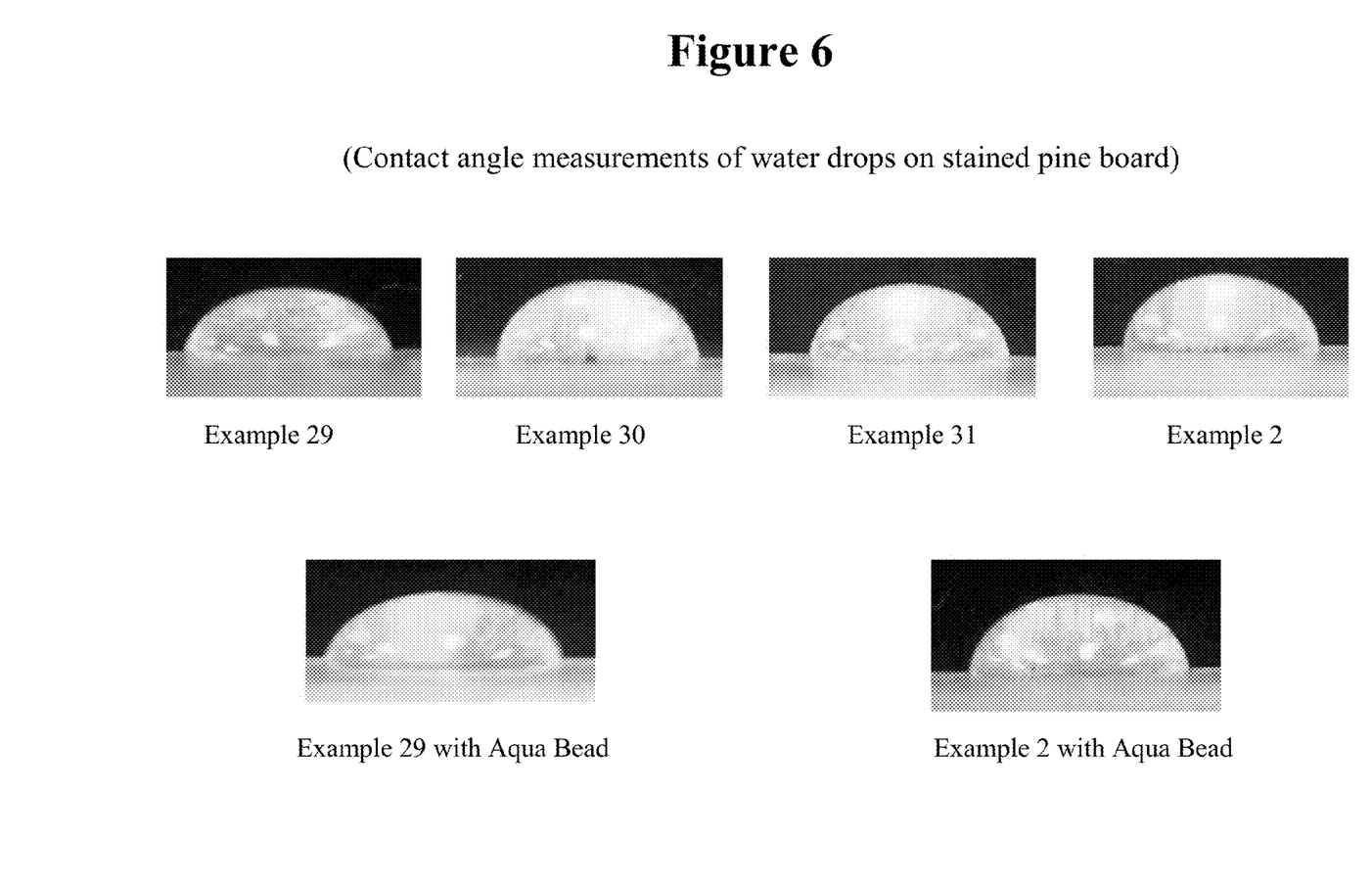
FIG. 6 describes the contact angle measurements of water drops on the stained pine board.

The next day a drop of water was placed on the top of each board. A photograph was taken and the contact angle was measured. The results are shown in FIG. 6. Higher water contact angles indicate a more repellent stain formulation.

| | Contact angle measurements | | | | | |
|---|---|---|---|---|---|---|
| | Surfactant in latex | | | | | |
| | Ex 29 | Ex 30 | Ex 31 | Ex 32 | Ex 29 with Aqua Bead | Ex 32 with Aqua Bead |
| Contact angle (deg) | 75 | 88 | 80 | 92 | 86 | 92 |

The contact angle of POE(4) nonylphenol sulfate, ammonium salt is the lowest and thus is the least water repellent coating. This is expected as the surfactant is not bound to the latex and is free to migrate to the air/coating interface lowering the surface tension of the drop. The other three latexes prepared with reactive surfactants demonstrate significantly higher contact angles with Example 32 having the highest contact angle. Comparison of the contact angles of Examples 31 and 32 shows that the second reactive group greatly improves the hydrophobicity of the coating.

The comparison between Examples 30 and 31 shows that the longer polyethylene oxide chain of example 31 reduces the contact angle and the hydrophobicity of the coating. Example 32, with the same length polyethylene oxide chain as Example 31 but having two reactive groups, has a much higher contact angle, even higher than Example 30, which has a shorter polyethylene oxide chain.

Upon addition of the Aqua Bead wax, the contact angle of Example 29 significantly increased, but not to the level of the two best surfactants without the Aqua Bead wax, the POE(10) allyl-substituted nonylphenol sulfate, $NH_4$ salt (Ex. 30) and Example 2 (in Ex 32 latex). This demonstrates the excellent water beading characteristics that polymerizable surfactants can impart to the latex. This may allow for less wax additives in the formula improving durability.

Odor of Stains

A simple odor test was performed on the final stains. The stains were placed into ½ pint cans and allowed to sit for 1 hour. The headspace was sampled and relative odor was assessed. The results are shown below:

Strongest odor Ex29>>Ex30>Ex31=Ex32 Weakest odor

The content of all references cited in the instant specifications and all cited references in each of those references are incorporated in their entirety by reference herein as if those references were denoted in the text While the many embodiments of the invention have been disclosed above and include presently preferred embodiments, many other embodiments and variations are possible within the scope of the present disclosure and in the appended claims that follow. Accordingly, the details of the preferred embodiments and examples provided are not to be construed as limiting. It is to be understood that the terms used herein are merely descriptive rather than limiting and that various changes, numerous equivalents may be made without departing from the spirit or scope of the claimed invention.

What is being claimed is:

1. A compound selected from the group consisting of:

(I)

where $R=CH_3$ or $CH_2CH_3$, n=1, 2, 3; x is 2-10, y is 0-200, z is from 5 to 40; Z can be either $SO_3^-$ or $PO_3^{2-}$, and $M^+$ is $Na^+$, $K^+$, $NH_4^+$, or an alkanolamine;

(II)

where $R=CH_3$ or $CH_2CH_3$, n=1, 2, 3; x is 2-10, y is 0-200, z is from 5 to 40;

(III)

where $R_1$ is a C10-24, alkaryl, alkenyl, or cycloalkyl, $R_2=CH_3$, $CH_2CH_3$, C6H5, or $C_{14}H_{29}$; x is 2-10, y is 0-200, z is from 5 to 40 Z can be either $SO_3^-$ or $PO_3^{2-}$, and $M^+$ is $Na^+$, $K^+$, $NH_4^+$, or an alkanolamine; and (IV)

where $R_1$ is a $C_{10-24}$ alkaryl, alkenyl, or cycloalkyl, $R_2=CH_3$, $CH_2CH_3$, $C_6H_5$, or $C_{14}H_{29}$; x is 2-10, y is 0-200, z is from 5 to 40.

2. A polymer latex incorporating therein one or more of the reactive surfactants of claim 1.

3. A coating formulation incorporating therein one or more of the reactive surfactants of claim 1.

4. A coating formulation incorporating the latex of claim 2.

5. The reactive surfactant composition of claim 1 wherein $R_1$ is selected from the group consisting of nonylphenol and tridecyl alcohol.

6. A UV curable coating formulation incorporating one or more of the reactive surfactants of claim 1.

7. A pigment dispersion incorporating one or more of the reactive surfactants of claim 1.

8. A pigment having incorporated therein one or more of the reactive surfactants of claim 1.

9. A titanium dioxide pigment incorporating therein one or more of the reactive surfactant of claim 1.

* * * * *